United States Patent [19]

Grulke et al.

[11] Patent Number: 5,046,486

[45] Date of Patent: Sep. 10, 1991

[54] COMPACT PULSING PUMP FOR IRRIGATION HANDPIECE

[75] Inventors: David H. Grulke, Battle Creek; Douglas L. Tyler, Sr.; William M. Booth, III, both of Paw Paw, all of Mich.

[73] Assignee: Stryker Corporation, Kalamazoo, Mich.

[21] Appl. No.: 297,841

[22] Filed: Jan. 13, 1989

[51] Int. Cl.⁵ ............................................. A61H 9/00
[52] U.S. Cl. ...................................... 128/66; 604/131
[58] Field of Search .................... 128/65, 66, 62 A; 604/33, 67, 131; 433/80; 239/99, 101, 102, 380, 381

[56] References Cited

U.S. PATENT DOCUMENTS

| | | | |
|---|---|---|---|
| 3,353,537 | 11/1967 | Knox et al. | 604/143 |
| 3,515,130 | 6/1970 | Tsujino | 604/70 |
| 3,561,433 | 2/1971 | Kovach | 128/66 |
| 3,768,472 | 10/1973 | Hodosh et al. | 604/143 |
| 3,993,054 | 11/1976 | Newman | 128/66 |
| 4,007,739 | 2/1977 | Bron et al. | 604/144 |
| 4,030,498 | 6/1977 | Tompkins | 604/152 |
| 4,061,142 | 12/1977 | Tuttle | 604/34 |
| 4,215,476 | 8/1980 | Armstrong | 433/80 |
| 4,278,078 | 7/1981 | Smith | 128/66 |
| 4,282,867 | 8/1981 | Du Toit | 128/66 |
| 4,515,532 | 5/1985 | Walling | 417/318 |
| 4,561,856 | 12/1985 | Cochran | 604/143 |
| 4,583,531 | 4/1986 | Mattchen | 128/66 |
| 4,655,197 | 4/1987 | Atkinson | 128/66 |
| 4,662,829 | 5/1987 | Nehring | 604/153 X |
| 4,776,840 | 10/1988 | Freitas et al. | 604/33 |

Primary Examiner—Robert A. Hafer
Assistant Examiner—Kevin G. Rooney
Attorney, Agent, or Firm—Flynn, Thiel, Boutell & Tanis

[57] ABSTRACT

A surgical pulsed irrigation handpiece comprises a pistol-like housing having a handle and a barrel extending forwardly from the top of the handle. A finger actuable trigger is provided on the handle front edge. An axially elongate pulsing pump extends longitudinally in the handle. An outlet tube extending from the top of the pump bends forwardly toward the front end of the barrel. The trigger controls pulsed liquid outflow from the pulsing pump through outlet tube. A preferred pulsing pump provides a piston axially slidable in a casing and a poppit axially slidable with respect to the piston. A first spring urges the piston rearward in the casing. A second spring urges the poppit forwardly with respect to the piston. A pumped liquid chamber in the casing ahead of the piston responds to piston reciprocation to provide a pulsed liquid outflow. The poppit responds to both piston travel and gas pressure in a motor chamber to pop open a gas exhaust port to terminate an irrigant liquid pulse and return the piston to a starting position.

27 Claims, 8 Drawing Sheets

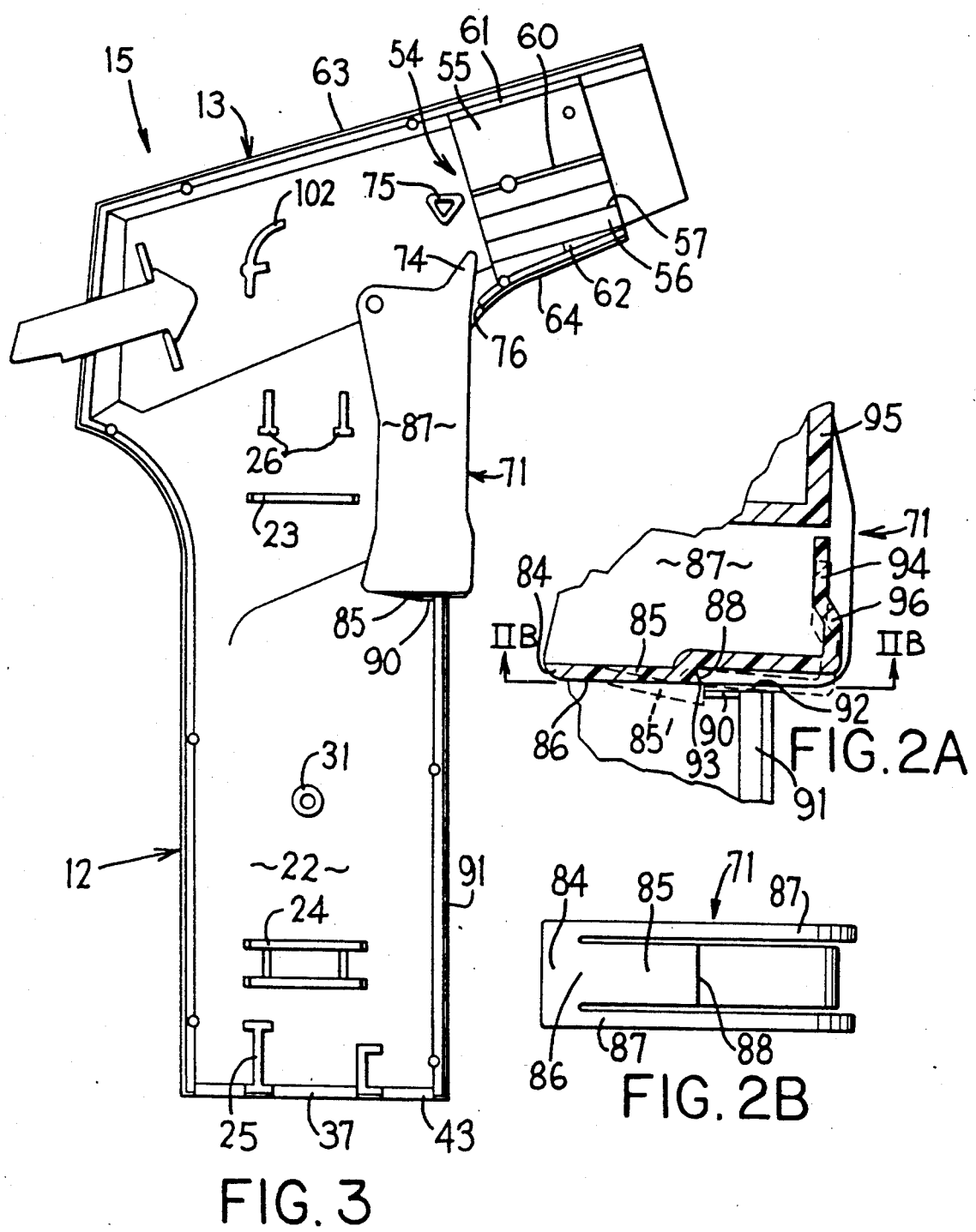

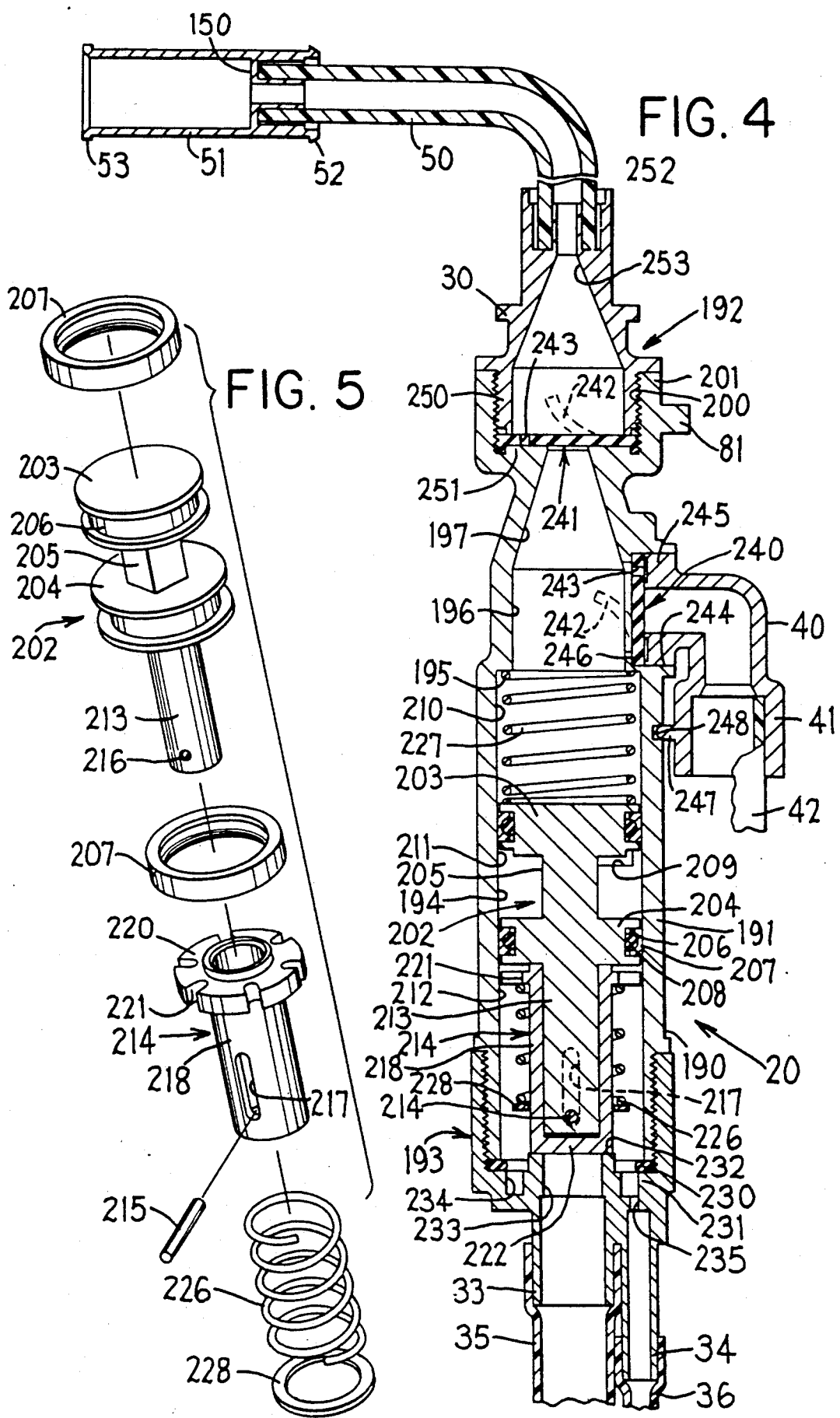

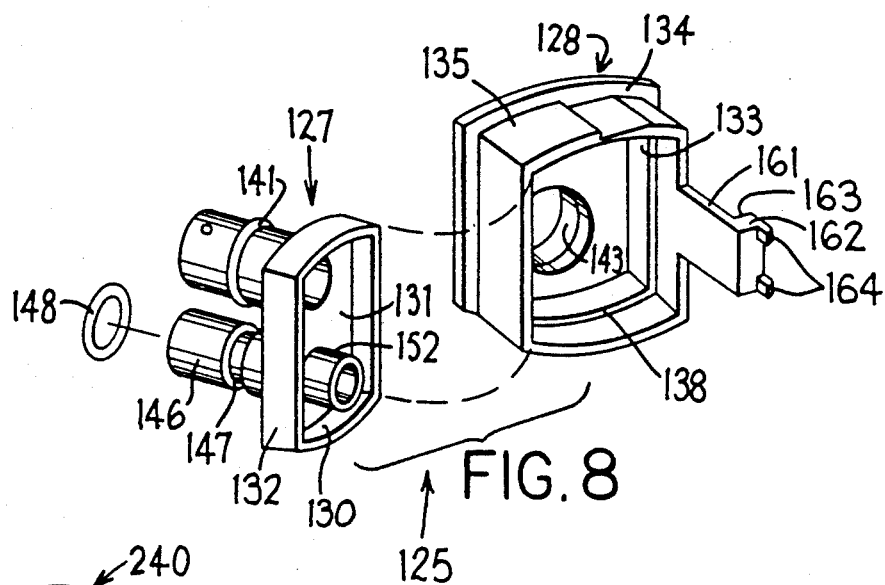
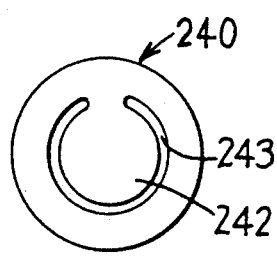
FIG. 4A
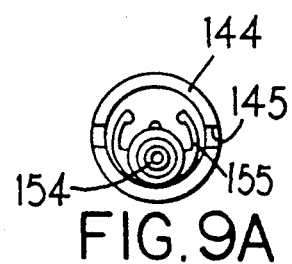
FIG. 9A
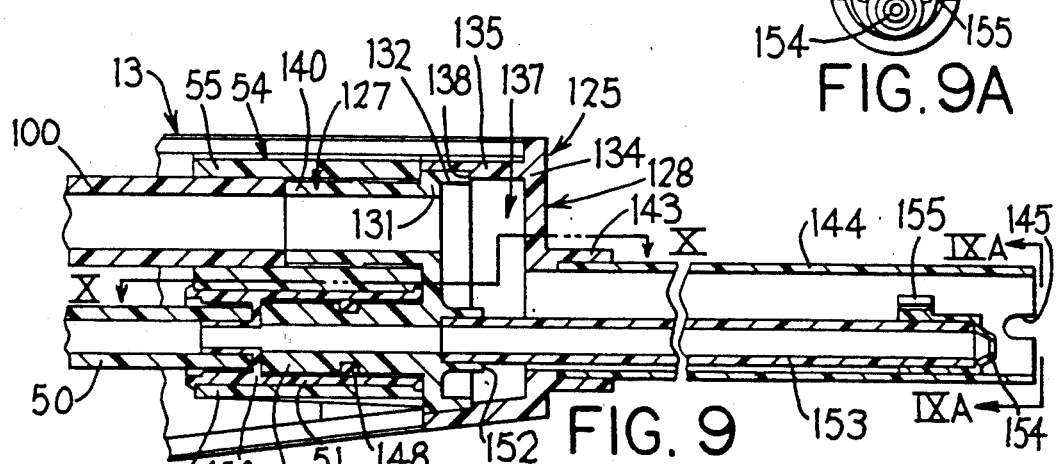
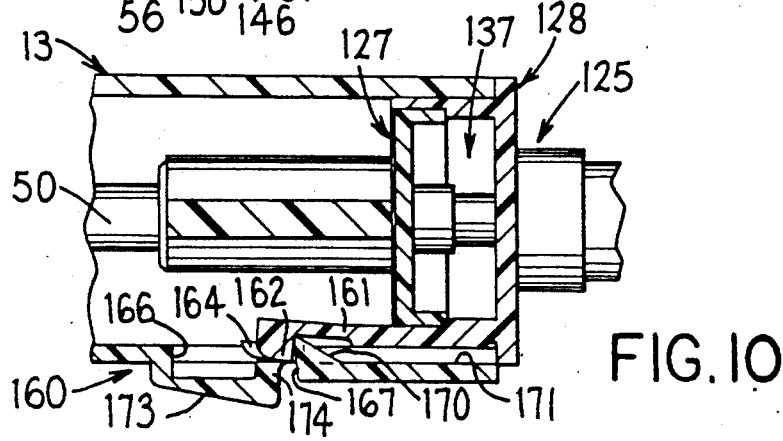
FIG. 10

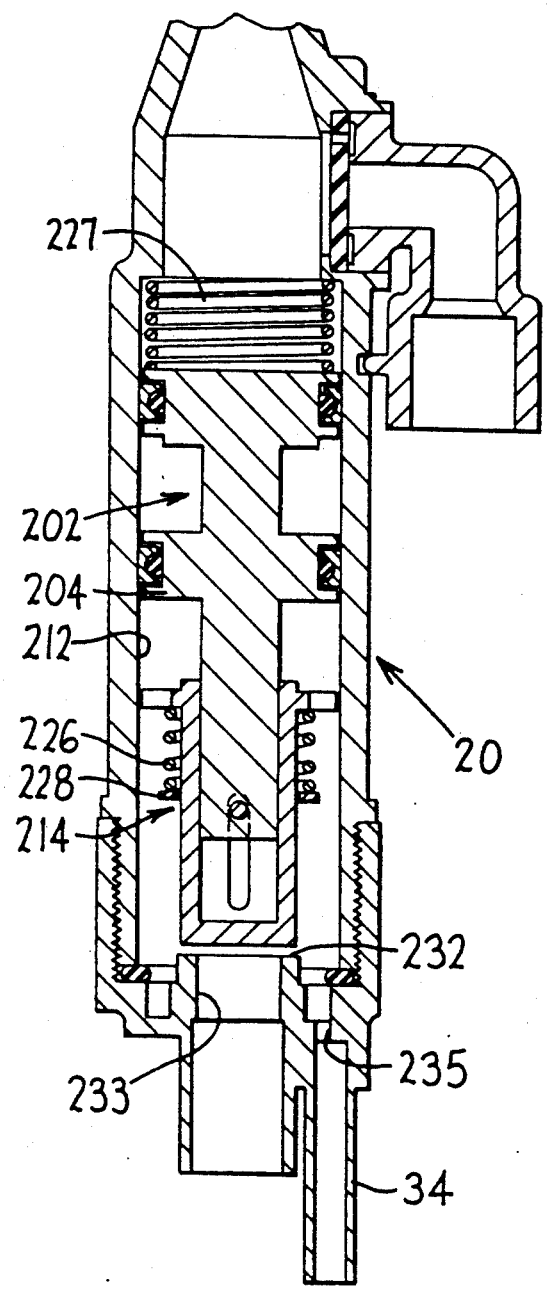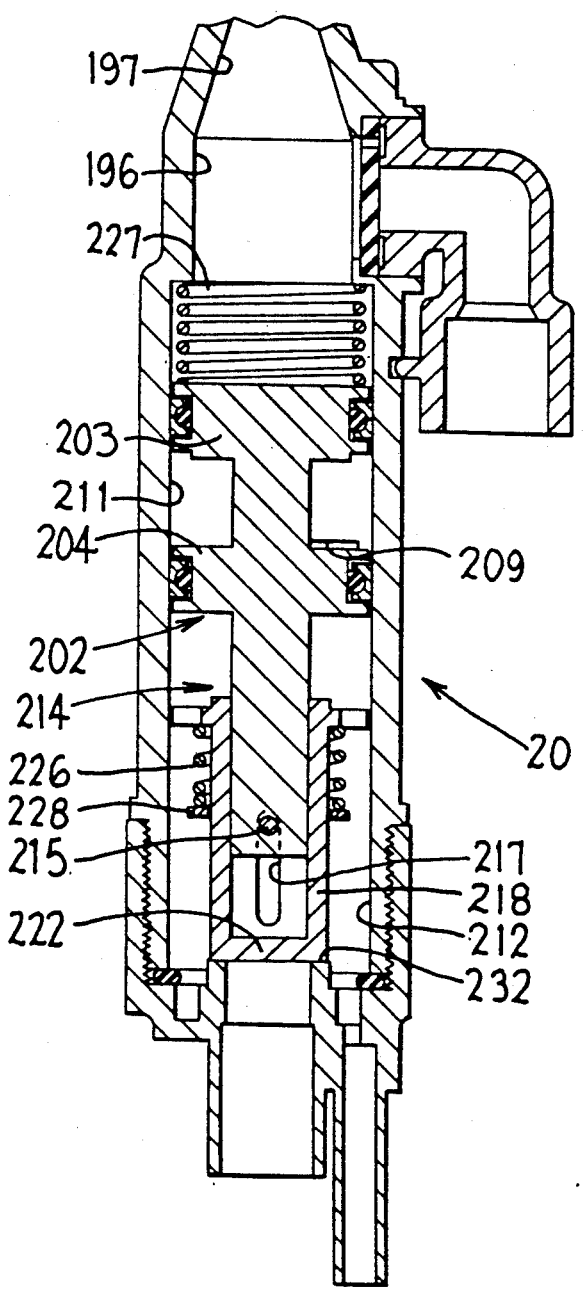

COMPACT PULSING PUMP FOR IRRIGATION HANDPIECE

FIELD OF THE INVENTION

This invention relates to a surgical irrigation handpiece and a pulsing pump therefor.

BACKGROUND OF THE INVENTION

Mattchen U.S. Pat. No. 4,583,531 discloses a hand held, pulsating jet, lavage usable for surgical purposes. A pressure air powered, reciprocating motor drives a reciprocating irrigant liquid pump to produce a pulsed irrigant liquid stream from the front of the barrel of the gun-shaped lavage. The motor is connected to a continuous source of pressure air.

However, the Mattchen motor and pump are separate and separable units, the pump unit being disposable and the motor unit being not. More particularly, in Mattchen the forward portion of the barrel hinges open for removal and replacement of the pump unit, the irrigant liquid supply tube and the pulsating irrigant liquid outlet tube. The top front portion of the barrel is hinged at the bottom front of the barrel, so as to tilt forwardly and allow upward removal of the mentioned pump unit and liquid supply and outlet tubes. The remainder of the apparatus, which is to be reused, comprises the motor unit and a relatively complex pressure air control valving system which is trigger operated to modulate the flow of pressure air to the motor and thereby control the pulsed irrigant liquid output flow indirectly. The construction complexity of the handpiece as a whole would appear to make it economically impossible to market as a disposable handpiece, and indeed the teaching of Mattchen on the point is clear. Accordingly, separate sterilizations of the pump unit, with its liquid hoses, on the one hand, and on the other hand the remainder of the handpiece, as well as the need to assemble and disassemble the two appear to add further to the cost and extra time required to use this system on an on-going basis.

Smith U.S. Pat. No. 4,278,078 (assigned to the assignee of the present invention) is pressure air powered and does provide a pulsing irrigant liquid outflow. However, the Smith unit is not in the handy form of a pistol, and is not a disposable tool. Further, irrigant liquid is supplied to the tool by gravity from an elevated storage container and passes through the tool in a resiliently compressible tube. A hammer reciprocated by an air motor repetitively pinches and unpinches the resilient tube to pulse the flow of irrigant liquid therethrough. The irrigant liquid pulses tend to have gradual, rather than sharp, start and stop characteristics. The apparatus does not "pump" from a liquid store located vertically below it.

Atkinson U.S. Pat. No. 4,655,197 discloses a handpiece providing a pulsating liquid flow for lavage use. However, pulsed irrigant liquid is applied to the handpiece from a remote pulsing source, in the form of a self-standing console. Liquid pulses may thus tend to become less sharp and well defined before they reach the handpiece.

Kovach U.S. Pat. No. 3,561,433 discloses a hand-held dental cleaning and massaging device. However, the Kovach device is in the form of a wand whose base includes both a small water reservoir providing the sole source of liquid and a $CO_2$ cartridge as the sole pressure gas supply. A trigger button shifts the valve core to permit pressurized water to flow from the outlet end of the wand. An undisclosed type of liquid pulsing device, of extremely compact size, joins the water outlet tube to the base portion of the wand. The only specific suggestion of a pulsing device given is that it may be a fluidic multivibrator or oscillator. The water supply is necessarily very small in volume and the pressure of the pressure gas is very high (as high as 900 PSI). The reliability and repeatability of the pulsing unit is unknown. The structure is relatively complex for its limited capability. Disposability appears neither to be taught nor economically feasible.

The objects and purposes of this invention include provision of a pulsed surgical irrigation handpiece and a self-contained motor/pump unit therefor, which apparatus is intended to be disposable after use and not to be reusable, which is producible as a sealed handpiece unit, which has a streamlined exterior free of tubes except at the base of the handle and at the forward end of the barrel, which is capable of incorporating and controlling suction as well as pulsed irrigant liquid, which has a self-contained motor/pump cartridge capable of producing sharp irrigant liquid pulses, which includes a "pop" pressure gas exhaust feature contributing to a rapid irrigant liquid pulse fall time, and which locates the motor/pump cartridge in the handle of the pistol-shaped handpiece to distribute weight between the handle and barrel of the handpiece and thereby provide a well-balanced hand tool.

Other object and purposes of the invention will be apparent to persons acquainted with apparatus of this general type upon reading the following description and inspecting the accompanying drawings.

SUMMARY OF THE INVENTION

A surgical irrigation handpiece comprises a housing having a handle and a barrel extending forwardly from the handle. A pulsing pump is disposed in the handle and has an outlet extending forward toward the front end of the barrel for supplying pulsed irrigant liquid to a surgical site.

A pressure gas powered, pulsed output, liquid pump comprises a piston axially slidable in a casing, a poppit axially slidable with respect to the piston for normally blocking exhaust of pressure gas from the casing and spring means associated with the piston and poppit.

BRIEF DESCRIPTION OF THE DRAWINGS

FIG. 2A is an enlarged fragment of the FIG. 2 trigger unit.

FIG. 2B is a bottom view of the FIG. 2A trigger.

FIG. 3 is a central cross-sectional view similar to FIG. 2 but with the pump/motor cartridge and suction tube removed to show the interior wall of the left housing part of the handpiece.

FIG. 4 is an enlarged central cross-sectional view of the motor/pump cartridge of FIG. 2.

FIG. 4A is a top view of the FIG. 4 upper flap valve.

FIG. 5 is an exploded pictorial view of the piston and poppit assembly of the FIG. 4 motor/pump cartridge.

FIG. 6A is a fragmentary central cross-sectional view similar to FIG. 5 but showing the piston in a forwardly advanced position on its forward most limit.

FIG. 6B is a view similar to FIG. 6A with the piston fully advanced forward and the poppit "popped" off the pressure gas exhaust port to exhaust pressure gas from the motor chamber.

FIG. 8 is an enlarged exploded pictorial view of the FIG. 1 tip unit, omitting the barrel extension of FIG. 9.

FIG. 9 is an enlarged central cross-sectional view of the FIG. 1 tip extension mounted in the end of the handpiece barrel.

FIG. 9A is a sectional view substantially as taken on the line IXA—IXA of FIG. 9.

FIG. 10 is a sectional view substantially as taken on the line X—X of FIG. 9.

DETAILED DESCRIPTION

Figure 1:
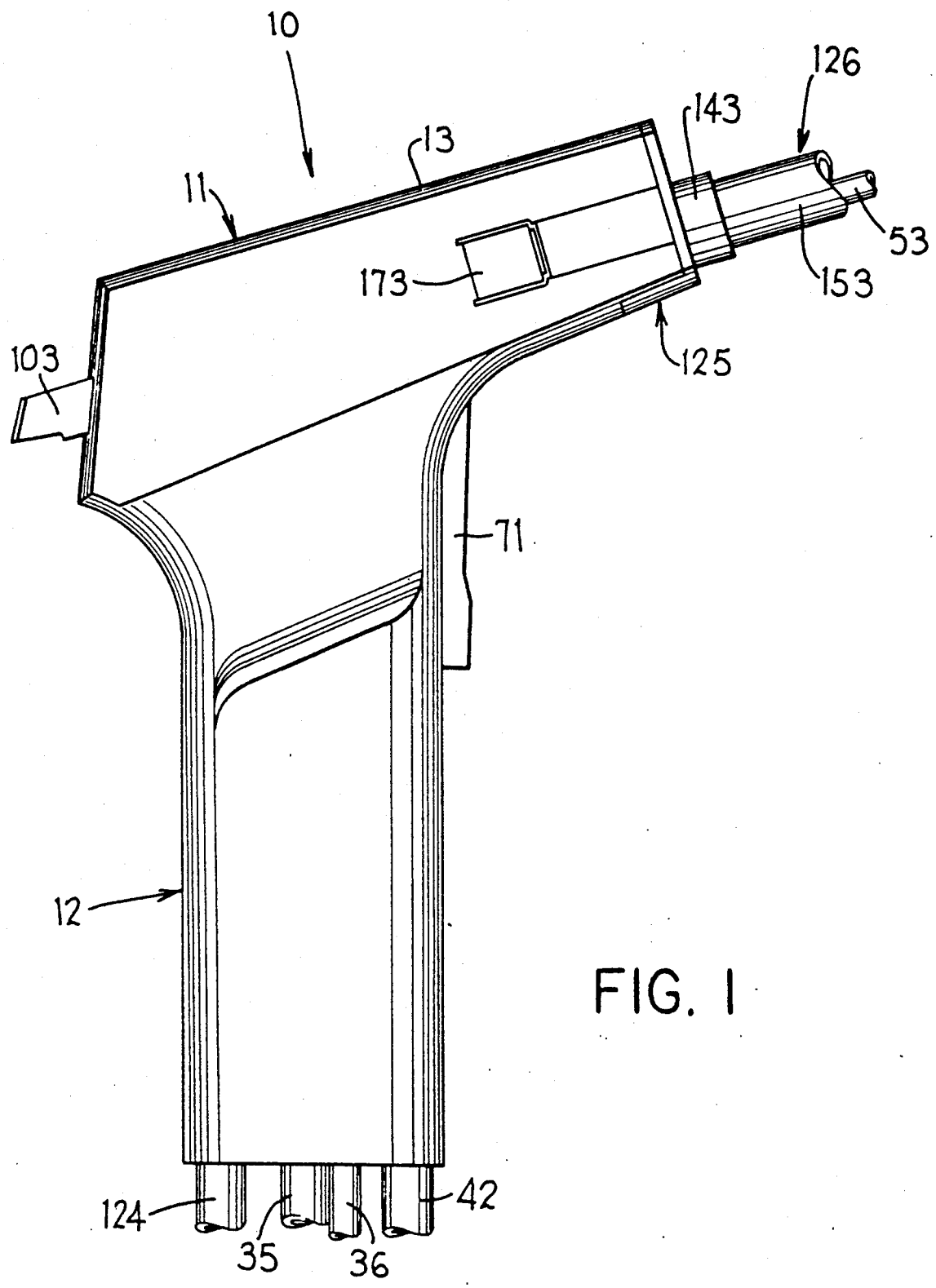
FIG. 1 is a right side elevational view of a surgical irrigation handpiece embodying the invention, with the trigger pulled to permit maximum pulsed irrigant liquid outflow.

Turning to FIG. 1, an irrigation handpiece 10 embodying the invention includes a generally pistol-shaped housing 11 including a butt, or handle, 12 engagable by the hand of the user and a barrel 13 integrally fixed atop the handle 12 and extending forward (rightward in FIG. 1) therefrom.

In the embodiment shown, the housing 11 comprises generally complimentary right and lefthand parts 14 and 15. The housing preferably is of molded plastic material, for example ABS. This facilitates not only formation of the outer shape of the housing, but also formation on the interial walls of the housing of a number of complexly shaped stubs, hereafter specifically discussed (some mirror imaged compliments and others not), usable to secure the right and left housing parts in fixed registration with each other and to locate the internal parts of the handpiece 10 in their working positions within the housing 11.

The right and left housing parts 14 and 15 are guided together by pin-like stubs 16 (FIG. 7) on the left housing part 15 which are received in a conventional manner in corresponding sockets (not shown) laterally opposed to the pin-like stubs 16. For the most part, the pin-like stubs 16 are disposed along the front, rear and top walls of the leftward housing part 15.

Attention is directed to the contents of the housing 11.

Figure 2:
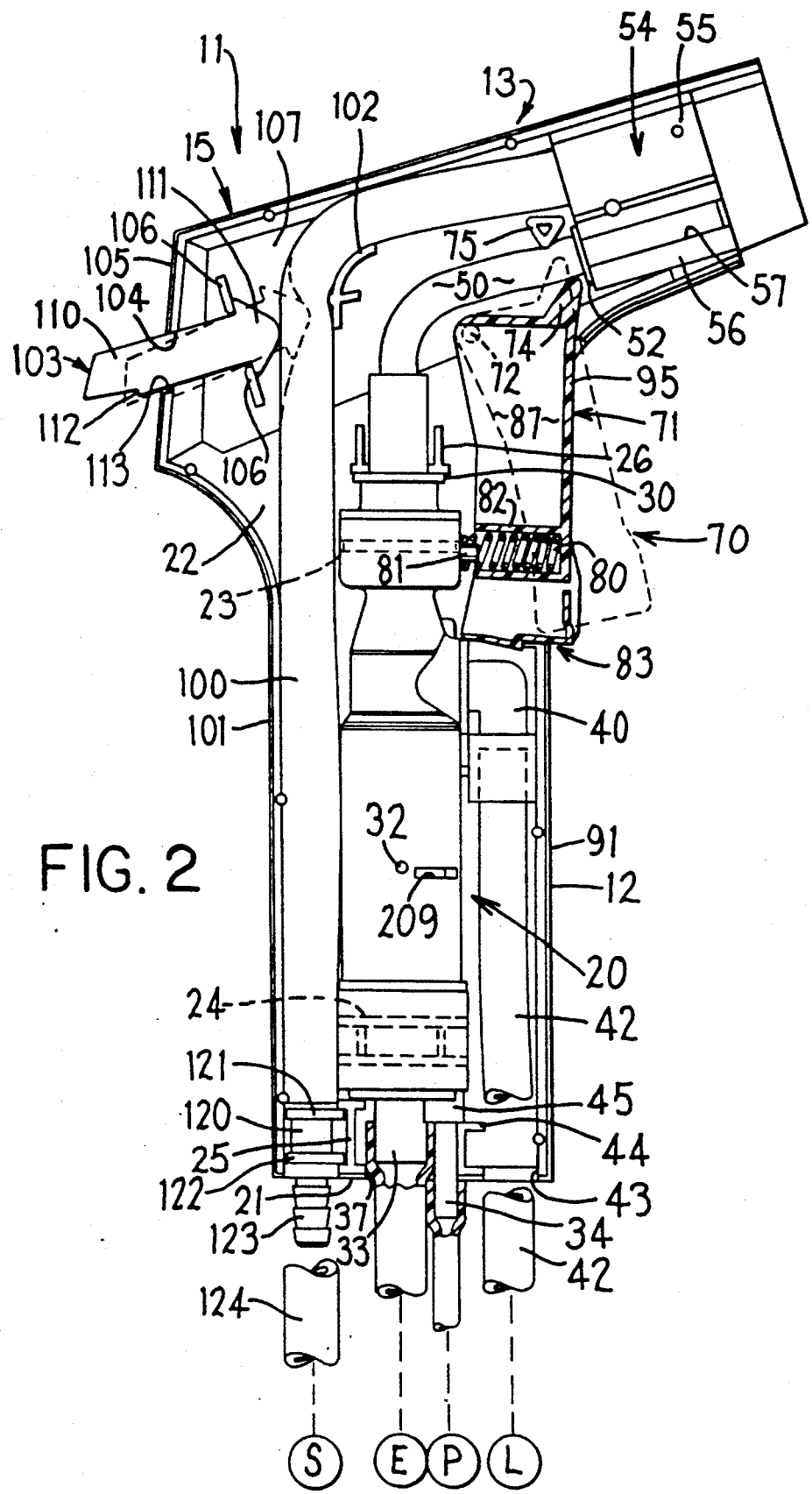
FIG. 2 is a central cross-sectional view of the FIG. 1 device showing alternate positions of the trigger and thumb button in broken lines.

A pressurized gas (preferably air) powered, pulsed outlet, liquid pump 20 (FIGS. 2 and 7) is located centrally in the handle 12 and extends likewise substantially from the bottom wall 21 of the handle upwardly therealong into the barrel 13. The pump 20 is aligned substantially parallel with the upstanding longitudinal axis of the handle 12. The right and left parts 14 and 15 of the housing 11 are concave and their opposed side walls 22 (FIGS. 2, 3 and 7) have similar, laterally opposed, concave, semi-circular upper and lower cradle stubs 23 and 24 (FIGS. 3 and 7), only those for the left housing part 15 being shown. The cradles 23 and 24 receive upper and lower parts of the pump 20 and locate same fixedly against lateral (right-left, and into-out of the page as seen in FIG. 2) movement with respect to the housing 11 with the right and left parts 14 and 15 assembled. The side walls 22 of the right and left housing parts 14 and 15 also fixedly support opposed T cross-section stubs 25 extending out from the bottom wall 21 of the housing, and a pair of laterally opposed inverted T cross-section stubs 26 located at the top of the handle 12. The stub 25 abuts the bottom of the pump 20 and the stubs 26 abut the top of a flange 30 near the top of the pump to fixedly locate the pump vertically therebetween. The pair of stubs 26 laterally (right to left in FIG. 2) locate an upper portion of the pump 20 snugly and fixedly therebetween to assist in lateral fixing of the pump. Again, it will be understood that similar stubs (not shown) on the right housing part 14 oppose the stubs 25 and 26 shown in FIG. 2 on the left housing part 15 for the same purpose. To further locate the pump against the right-left movement in FIGS. 2, 3 and 7, a cup-like stub 31, fixed on the inner face of the side wall 22 of the left part 15, receives a small lateral projection 32 (like that on the right side of the pump in FIGS. 2 and 7) on the left side of the pump 20 in a snug manner.

Extending downward from the bottom of the pump 20 are a central tubular fitting 33 (FIGS. 2 and 7) and an eccentrically located, stepped, elongate tubular fitting 34 offset forwardly (rightwardly in FIG. 2) of the fitting 33. Fittings 33 and 34 are male hose fittings which snugly and slidably receive thereover the upper ends of respective gas exhaust and pressure gas supply hoses 35 and 36. The hoses 35 and 36 are conventional, clear, soft, resilient plastic hoses. The exhaust hose fitting 33 is of substantial larger diameter than the pressured gas hose fitting 34. The exhaust fitting 33 here terminates just above the bottom wall 21 of the housing while the reduced diameter bottom end of the fitting 34 extends downwardly through the bottom wall 21. Opposed recesses 37 in the housing parts 14 and 15, namely at central portion of the bottom wall 21 form, in the assembled housing 11, an opening through the bottom wall, through which the reduced diameter lower extremity of the pressure gas fitting 34 snugly extends, and through which the gas exhaust hose 35 can upwardly extend to sleeve over its fitting 33. The opposed recesses thus form a very approximately keyhole shaped opening.

Figure 7:
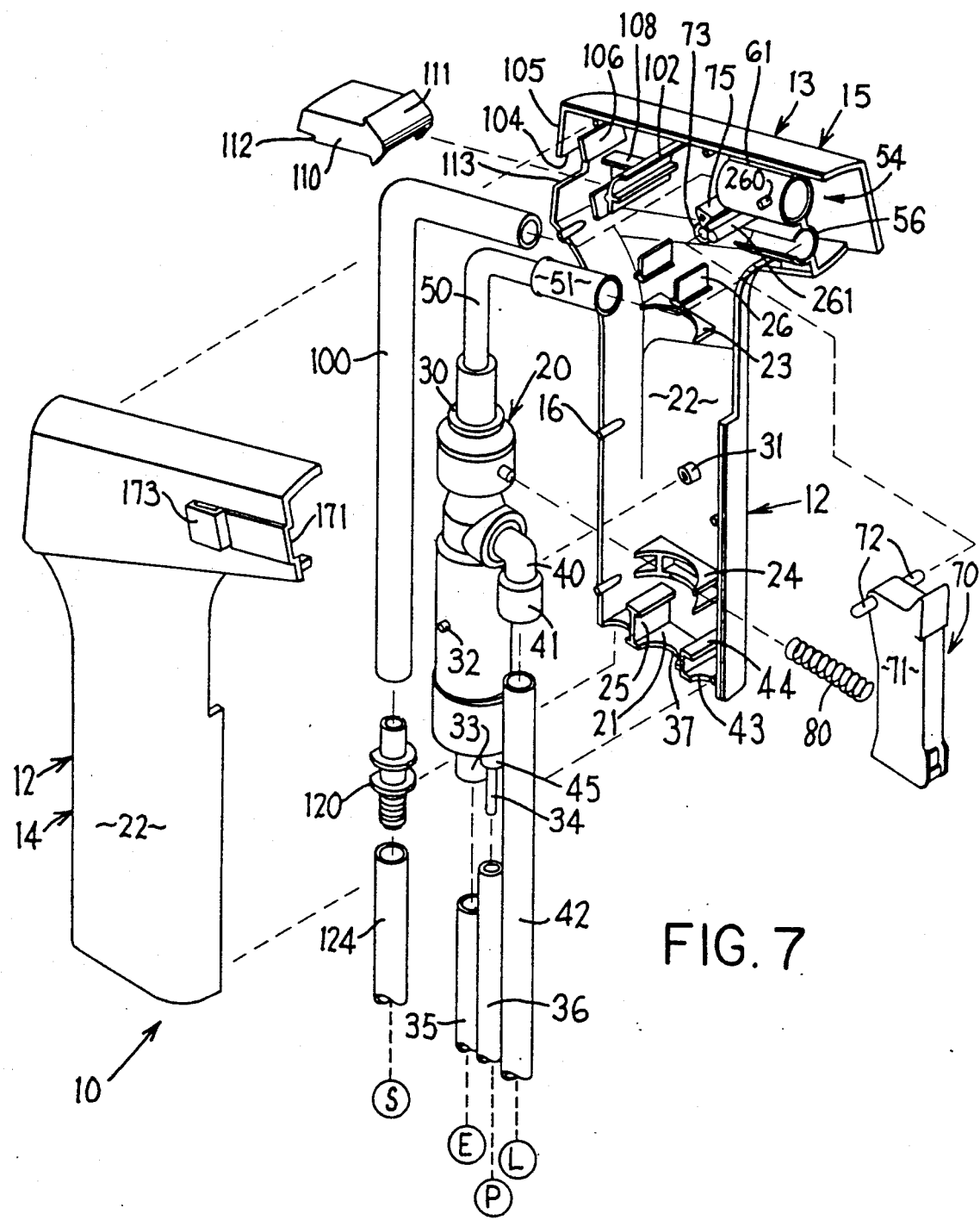
FIG. 7 is an exploded pictorial view of the FIG. 1 handpiece.

An inlet liquid fitting 40 (FIGS. 2 and 7), here in the form of a 90° elbow, extends forwardly and downwardly from the front face of the pump 20 at a point intermediate the top and bottom ends thereof. The lower end of the fitting 40 is belled at 41 to form a female fitting end for snugly receiving therein the upper end of an irrigant liquid supply hose 42 (FIG. 7). The irrigant liquid supply hose 42 extends downward from the belled mouth 41 of the fitting 40 through an opening in the bottom wall 21 of the housing formed by opposed semi-circular recesses 43 in the right and left housing parts 14 and 15. Inverted L cross-section stubs 44, fixedly laterally protruding from the interior of the side walls 22 of the right and left housing parts 14 and 15, oppose and extend toward each other and are located laterally between the fitting 34 and liquid inlet hose 42. The stubs 44 snugly abut the front face of the fitting 34 and support the stepped fitting 34 at its downwardly facing step, i.e., support the enlarged upper portion 45 of the pressure gas inlet fitting 34.

A pulsed irrigant liquid outlet tube 50 (FIGS. 2 and 7) extends upward from the top of the pump 20 into the barrel 13 and then angles forwardly along the barrel 13. In one unit built according to the present invention, the hose 50 was of a type provided with a flexible waterproof core and braided fabric exterior for a long working life despite repeated pinching of the tube to throttle the flow from the pump 20.

A tubular front end fitting 51 (FIGS. 4 and 7) is fixed to the front end of the hose 50 as seen in FIG. 4. The front end fitting 51 is rigid and has relatively small radially outwardly extending flanges 52 and 53 at the ends thereof.

A two-cylinder over-under bracket 54 (FIGS. 3 and 7) is aimed lengthwise of the barrel 13 and is fixed near the front (rightward) end of the barrel. The bracket 54 comprises an upper cylinder 55 to the underside of which is fixed a parallel lower cylinder 56 which has a length extending slot 57 to give it sufficient circumferential resilient expandability to enable longitudinal insertion of the hose 50 and tubular front end fitting 51 rearwardly therethrough prior to insertion of the lower end of the hose 50 into the top end of the pump 20. In this way, the front end of the liquid outlet hose 50 is rigidly fixed with respect to the barrel 13. The upper and lower cylinders 55 and 56 are fixed rigidly to each other by an integral web 60 (FIG. 3). Similar webs 61 and 62 fix the top of upper cylinder 55 to the top wall 63 of the barrel 13 and fix the lower cylinder 56 to the bottom front wall 64 of the barrel 13, respectively. The webs 60-62 are here in a common vertical plane substantially at the plane of demarcation between the right and left housing parts 14 and 15, the webs 61 and 62 being on the left housing part as seen in FIG. 7.

A trigger unit 70 (FIGS. 2 and 7) comprises a hollow, boxlike trigger 71 which is open on its rear edge adjacent to the pump 20. Coaxial pivot pins 72 are fixed to and extend toward the right and left housing parts 14 and 15 from fixed location on the upper rear corner of the trigger 71. The pivot pins 72 are pivotally received in laterally opposed bosses 73 fixed to the inner surfaces of the side walls 22 of the right and left housing parts.

A spur 74 upstands from the upper right corner of the trigger 71 and in the pulled-in position of the trigger 71 shown in FIGS. 2 and 3, the spur 74 lies close below the hose 50 and behind the lower cylinder 56 so as not to interfere with either one thereof. A triangular cross-section anvil 75 projects rigidly from the interior face of the side wall 22 of the left housing part 15 in contact with the top of the hose 50. Both the spur 74 and anvil 75 are of rounded-point cross-section adjacent the hose 50, so as to progressively compress the hose 50 therebetween as the trigger 71 pivots forwardly from its solid line position to its dotted line position shown in FIG. 2. With the trigger in its full forward dotted line position of FIG. 2, liquid flow through the hose 50 is completely shut off. The trigger 71 is located in a window 76 (FIG. 3) in the upper front wall of the handle 12, the window being sized to permit the trigger 71 to freely swing between its rear and front positions shown in FIG. 2.

A helical compression spring 80 (FIG. 2) continuously resiliently urges the trigger 71 toward its forward dotted line position of FIG. 2. The spring 80 is of sufficient strength to shut off liquid flow through the hose 50. On the other hand, a human operator can easily overcome the force of the spring 80 to pull the trigger 71 rearward and hold it in any desired position between its dotted line and solid line limiting positions in FIG. 2. The spring 80 rests at its opposite ends on the front face of the upper portion of the pump 20 and on the rear face of the front wall of the trigger 71. The spring 80 is trapped by snugly sleeving over a pin-like forward projection 81 on the front face of the pump 20 and by being snugly but slidably received in an axially elongate well 82 which projects rearward from the front wall of the trigger 71 substantially to the rear edge of the trigger.

The trigger 71 can be locked in its rearward solid line position FIG. 2, to permit maximum continuous irrigation liquid flow through the hose 50, without need to manually continuously pull the trigger 71 rearwardly, by a resilient latch unit 83 shown in FIGS. 2, 2A, and 2B. More particularly, the mid and forward portions of the trigger bottom wall 84 form a tongue 85 which is integrally and resiliently hinged at 86 to the rear part of the bottom wall 84 and extends forward therefrom. The side edges of the tongue 85 are separated by fore-aft slots (FIG. 2B) from the side walls 87 of the trigger 71. The tongue 85 normally barely clears the bottom edge 92 of the window 76 in the front wall 91 of the handle 12, in the manner shown in solid line in FIG. 2A. A forward facing, forwardly concave step 88 intermediate the front and rear ends of the tongue 85 is located to trap therein the rear edge of a small flange 90 projecting rearwardly from the front wall 91, flush with the bottom window edge 92, when the tongue 85 is manually bent downward at the resilient integral hinge 86 to its lowered dotted line position 85' of FIG. 2A. In this lower position, the small forward projecting lip 93, formed by the cavity of the forward facing step 88, becomes trapped beneath the flange 90, so as to hold the tongue 85 latched in its downward dotted line position 85' and accordingly to positively block the trigger 71 from forward movement out of its rearward limiting position shown in solid lines in FIGS. 2, 2A, and 3, namely in a position where its spur 74 does not interfere with flow through the hose 50.

The tongue 85 has integrally fixed to its front end an upstanding front wall 94 which normally is substantially flush with the front wall 95 of the trigger 71. A rearward pull on the trigger 71, by reason of user finger pressure on the front wall 95 thereof, will move the rearward located trigger 71 slightly further to the rear sufficient to disengage the lip 93 from the flange 90 and let the tongue 85 and front wall 94 thereon resiliently spring upward from their dotted line position to their solid line position in FIG. 2A, such that the trigger 71 is no longer latched to the front wall 91 of the handle 12. Thereafter, relaxing the rearward user finger force on the trigger 71 will allow the trigger 71 to pivot forwardly under the force of the spring 80 to progressively compress the hose between the spur 74 and anvil 75 and thus progressively reduce, to zero, irrigant liquid flow through the hose 50.

On the other hand, when it is desired to latch the trigger 71 in its rearward, hose 50 open, position shown in solid lines in FIGS. 2 and 3, the operator's fingers pull the trigger 71 rearward to its rearward limit wherein the lip 93 is above and slightly to the rear of the flange 90. At that point, downward pressure of a finger of the user on the forward bulge 96, near the bottom of the tongue front wall 94, depresses the tongue 85 from its solid line position to its dotted line position 85 wherein the lip 93 lies below the flange 90. A slight relaxation of the rearward force on the trigger allows the trigger to move forward slightly, enough to trap the flange 90 within the forwardly concave step 88 of the tongue 85, with the lip 93 remaining trapped below the flange. In this way the trigger 71 is restored to its latched position shown in FIGS. 2 and 3 (and in dotted line in FIG. 2A), with the hose 50 open for full flow.

In the embodiment shown, the handpiece 10 is adapted to provide suction as well as pulsed irrigation at a surgical site. Thus, a flexible suction hose 100 (FIGS. 2 and 7) extends from near the bottom wall 21 of the handle upward snugly between the pump 20 and rear wall 101 of the handle and upward into the top portion of the barrel. The suction hose 100 bends in a curved manner forward over a generally "f" shaped anvil 102 and hence forward to seat within the rear end portion of the upper cylinder 55 of the over-under bracket 54.

A thumb button 103 (FIGS. 2 and 7) is generally rectangular in configuration (and in the embodiment shown open downwardly). The thumb button 103 is partially housed in the rear end portion of the barrel 13. The rear end portion of the thumb button 103 extends snugly but slidably through a rectangular window 104 in the rear wall 105 of the barrel. The front portion of the thumb button 103 is snugly slidably guided between a coplaner pair of plate stubs 106 fixedly protruding from the inner face of the side wall 107, in opposed coplaner pair of similar plate-like stubs protruding from the opposed side wall of the right housing part 14 toward the mentioned stubs 106 on the left housing part 15. The thumb button 103 is thus guided for movement by the window 104 and the stubs 106 for sliding movement generally along the length direction of the barrel 13. Opposed stubs 108 (FIG. 7) are fixed to and protrude toward each other from the barrel side walls of the right and left housing parts 14 and 15. The stubs 108 slidably bear against the opposite sides 110 of the thumb button 103 to prevent side to side pivoting of the thumb button. The front end of the thumb button 110 is defined by a vertically enlarged, forward tapering head 111, which from the side looks much like an arrowhead with a rounded point. The vertical enlargement of the head 111 prevents the thumb button from being pulled rearward beyond its solid line position shown in FIG. 2, by interfering with the front faces of the plate-like stubs 106.

By pushing the thumb button 103 forward, by means of the thumb of the user, the head 111 is pushed forward toward the anvil 102 and thus progressively compresses the suction hose 100 therebetween to progressively reduce suction at the front end of the hose 100. With the thumb button 103 in its forward-most position shown in dotted line in FIG. 2, the suction tube 100 is closed, between the head 111 and anvil 102.

The rear bottom portion of the thumb button 103 is relieved to form a rear facing step 112. By pushing the thumb button forward and downward at its exposed rear end, the bottom of the thumb button rides along the bottom edge of the window 104 until the step 112 passes forward through the window and drops down over the bottom edge of the window 104 to its dotted line position in FIG. 2. In that position, the step interferes with the bottom edge 113 of the window 104 to latch the thumb button 103 in its forward, dotted line, hose closed position to hold off suction at the forward end of the hose 100 without need to continue manual pressure on the thumb button 103. To release the thumb button, the user merely lifts the exposed rear end of the thumb button 103, for example by flicking it upward with his thumb, whereupon the inherent resilience of the resilient suction hose 100 forces the thumb button 103 back to its retracted solid line rest position of FIG. 2, opening the suction hose to full flow.

In the embodiment shown, the bottom (FIGS. 2 and 7) of the suction hose 100 has telescoped therein the upper end of a conventional tube connector 120. The mid portion of the tube connector 120 is spool-shaped, with upper and lower flanges 121 and 122 which are gripped between the top of the T-shaped stub 25 and bottom wall 21 of the handle 12 to fix the bottom of the suction hose 100 within the housing 11. The ridged lower end 123 of the tube connector 120 is releasibly telescopingly received in the adjacent end of a conventional external flexible suction tube 124.

The suction tube 124 leads to a suitable conventional suction source S. Similarly, the external gas exhaust tube 35, pressure gas supply tube 36 and liquid supply tube 42 are connectable at their remote ends to a conventional exhaust facility E, gas pressure (preferably air pressure) source P, and irrigant liquid source L, as schematically indicated in FIG. 7. In the preferred embodiment shown, the exhaust facility is not conventional but rather takes the form of a special exhaust sound muffler hereafter described.

A tip unit 125 (FIGS. 1 and 8-10) is releasably mounted on the front of the barrel 13 and extends forward therefrom. The tip unit 125 shown mechanically transforms the means for providing suction and pulsed irrigant liquid, from the parallel resilient hoses 50 and 100 within the barrel 13, to form a single ridge of clear plastic barrel extension 126 (FIG. 9) which can be inserted into the area of a wound during surgery for providing suction and/or pulsed irrigant liquid flow.

Interposed between the barrel extension 126 and the barrel 13 the tip unit 125 includes rearward facing insert 127 telescoped partly in a body 128 (FIGS. 8 and 9).

The insert 127 has a forward facing recess 130 defined by a rear wall 131 from which extends forwardly a perimeter flange 132. The body 128 has a rearwardly facing recess 133 defined by a front wall 134, rearwardly from which extends a perimeter flange 135. In the embodiment shown, the front wall 134 extends radially beyond the perimeter flange 135 both sidewardly and upwardly. The body perimeter wall 135 has a rearward facing internal step 138 (FIG. 8). The perimeter flange 132 of the insert 127 is inserted forwardly into the recess 133 in the body 128 until it comes to rest against the step 138, in which the position it is fixed, by any convenient means such as adhesive bonding. The result is that the communicating recesses 130 and 133 form an approximately rectangular suction chamber 137 (FIGS. 9 and 10).

A hollow suction boss 140 extends integrally rearwardly from the rear wall 131 of the insert 127. The boss 140 has an external annular rib 141 and small bumps 142 by which it is guided into snug, substantially sealed relation in the upper cylinder 55 of the over-under bracket 54 adjacent front end of the barrel 13 (FIG. 9). When thus releasably inserted, the rear face of the front wall 134 of the body 128 abuts the front end of right housing part 14 and left housing part 15 and the rear end of the suction boss 140 lies adjacent the front end of the suction hose 100.

A hollow suction boss 143 extends fixedly forward from the front wall 134 of the body 128. Stepped within the boss 143 is an elongate, forward extending, large bore tube 144, here equipped with a forwardly opening, U-shaped diametral slot 145 at the front end thereof. The large tube 144 defines the external part of the barrel extension 126. In this way, the suction path extends forward from the hose 100 through the boss 140, suction chamber 137, boss 143 and large tube 144 to conveniently bring suction to any desired position of the surgical site.

As seen in FIG. 9, the suction boss 140 is offset vertically above the suction boss 143 so that the suction chamber 137 provides a vertical transition in flow.

A hollow irrigant liquid boss 146 (FIGS. 8 and 9) fixedly extends rearwardly from the rear wall 131 of the insert 127 in spaced relation below the suction boss 140. The liquid boss 146 is annularly grooved at 147 to receive an O ring 148. The liquid boss 146 with its O ring 148 is snugly and sealingly received in the free end of the fitting 51 on the front end of the pulsed irrigant liquid hose 50 (FIGS. 4 and 7), which in turn is clamped in the generally C-shaped cross-section lower cylinder 56 of the over-under bracket 54 at the forward end of the housing barrel 13. The radial web 150 within and intermediate the ends of the fitting 51 supports a rearward extending nipple 151 (FIG. 4) over which the front end of the hose 50 is snugly and sealingly seated. The liquid boss 146 extends substantially to the web 150. A further liquid boss 152 extends fixedly forward from the rear housing wall of the insert 127, in coaxial communication with the liquid boss 146. A small diameter irrigation tube 153 of rigid, preferably clear, plastic material is seated in its rear end sealingly in the boss 152 and extends forward therefrom along the bottom portion of the large tube 144. The irrigation tube 153 is substantially smaller in diameter than the large tube 144 and is located eccentrically therein, namely below the central axis thereof. The front end of the irrigation tube 153 is snugly received in and sealed with respect to a restrictive nozzle 154 located just inboard of the forward end of the large tube 144 and aimed forwardly through the open front end of the large tube 144. The nozzle 154 is of resiliently flexible plastic material and includes sidewardly extending resiliently bendable wings 155 resting within the suction tube 144 to help stabilize the forward end of the irrigation tube 153.

The tubes 153 and 144 together form the barrel extension 126.

The tip unit 125, comprised of the insert 127 fixedly telescoped in the body 128 and the barrel extension 126 extending forwardly therefrom are releasably inserted in the front end of the barrel 13 as follows. The bosses 140 and 146 are telescopingly received, as above discussed, in the upper barrel 55 and fitting 51 (in turn received in the lower barrel 56 of the housing 11). In addition, the top and sides of the perimeter flange 135 of the body 128 are snugly but slidably received in the front end of the barrel 13, and the rear face of the front wall 134 of the body 128 abuts the front face of the right housing 14 and left housing 15. In this way, the barrel extension 126 is located rigidly with respect to the barrel 13 and projects forwardly therefrom. To prevent the tip unit 125 from inadvertently escaping forwardly from the front end of the barrel 13, the two are connected by a latch unit 160 (FIG. 10). A tongue 161 (FIG. 8) extends rearwardly from the right side of the perimeter flange 135 of the body 28. The tongue is resiliently bendable toward the vertical central plane of the tip unit 125 (toward the point of the axis of the bosses 140 and 146). The rear end of the tongue 161 has a laterally outboard flange 162 defining a forward facing latch step 163. Rearwardly and outwardly facing ramp fingers 164 extend rearward from the outboard face of the flange 162. The right side of the barrel 13 has a latch opening 166 (FIG. 10) therethrough which defines a rear facing latch step 167 in part defined by a forwardly and laterally inwardly facing ramp 170. Upon insertion rearwardly of the tip unit 125 into the front end of the barrel 13, the ramp fingers 164 enter a forwardly extending and laterally inwardly facing longitudinal groove 171 in the inner surface of the right half of the barrel 13. Continued rearward insertion of the tip unit 125 into the front end of the barrel 13 causes the ramp fingers 164 to slide to the rear end of the groove 171, and climb laterally inward along the ramp 170, thereby bending the tongue 161 laterally inward. Eventually, as the tip unit 125 reaches its fully inserted position within the barrel 13, the flange 162 slides over the rearward tip of the ramp 170 and resiliently latches over the step 167 to achieve the latched position shown in FIG. 10. Interference between the flange 162 and step 167 positively precludes the tip unit 125 from being withdrawn forwardly from the front end of the barrel 13.

When it is desired to withdraw the tip unit 125 from the front end of the barrel 13, the operator simply presses laterally inward a release lever 173 accessible on the right side of the barrel 13. The release lever 173 is integrally hinged (bendably connected) at its rearward end to the right side wall of the barrel 13. The front end of release lever 173 is provided with a laterally inward protrusion 174 laterally facing the flange 162 on the tongue 161. Thus, to release the tip 125 from the barrel 13, the operator simply presses laterally inward the release lever 173 to pivot the protrusion 174 inward sufficient to displace the flange 162 laterally inward of the step 167. The tongue 161 thus being freed from the step 167, the tip unit 125 is free to be pulled forwardly out of the front end of the barrel 13.

Turning now to a preferred embodiment of the pump 20, attention is directed to FIGS. 4 and 5. The pump 20 comprises an elongate hollow pump casing 190 comprising an open ended cylindrical body 191 and top and bottom end caps 192 and 193. The casing 190 contains an elongate cylindrical circular cross-section main bore 194. The downward (rightward in FIG. 4) facing step 195 separates the main bore 194 from a short, upper, circular cross-section, cylindrical bore 196. The bore 196 is continued upward (FIG. 4) by a frustoconical portion 197. The upper end of the frustoconical portion 197 communicates with a recess 200 in the upwardly opening, cup-shaped upper end 201 of the casing 190.

A piston 202 is axially slidable in the main bore 194. The piston 202 is a one-piece generally spool-like member comprising an upper pumping head 203 and a lower pressure gas motor head 204 of the same diameter. The heads 203 and 204 are axially spaced by an integral, reduced square cross sectional portion 205. Each of the piston heads 203 and 204 has an annular groove 206. An annular slipper seal 207 is seated in the groove 206 in each head. In the embodiment shown, the slipper seals 207 are of U-shaped cross-section opening concavely radially inward, with an O ring 208 sandwiched radially between the slipper seal and the bottom of the corresponding piston groove 206, the O ring 208 being received in the radially inwardly opening concave face of the slipper seal 207. The slipper seals 207 permit up and down sliding motion of the piston 202 while preventing fluid leakage axially past each piston head 203 and 204. The piston heads 203 and 204 divide the bore 194 into three axially spaced chambers, namely an upper liquid chamber 210 which extends into the bore 196 and frustoconical portion 197, a middle leakage gas escape chamber 211 and a lower pressure gas chamber 212.

The middle chamber 211 opens through a vent 209 (FIG. 4) in the side of the casing body 191. Thus, the middle chamber 211 is continuously vented to the interior of the handpiece housing 11 and thereby, through the several openings in such housing, to the exterior. The vent 209 is positioned vertically to continuously communicate with the space between the piston heads 203 and 204 throughout the permitted vertical travel of the piston. Thus, should any leakage of pressurized gas unexpectedly occur upward past the seal 207 on the pressure gas motor head 204, such pressure gas will be vented at 209. This positively precludes a buildup of gas pressure in the middle chamber 211 between the piston heads 203 and 204 and thereby positively precludes any possible leakage of pressurized gas upward past the seal on the pumping head 203 and into the irrigant liquid in the upper chamber 210 extending vertically above the pumping head 203 through the bore 196 and frustoconical portion 197.

The piston 202 has a coaxial, reduced diameter, cylindrical tail extending below the pressure gas motor head 204 into the pressure gas chamber 212. An axially elongate, cylindrical, generally cup-shaped poppit 214 is axially slidably sleeved snugly over the tail 213 in the pressure gas chamber 212. The internal depth of the poppit 214 is substantially equal to the axial length of the tail 213.

The poppit 214 has a radially extending flange 220 near its upper end which extends close to but clears the inner wall of the bore 194. Axial passages 221 in the flange 220 permit free gas flow axially past the flange 220. The poppit has a closed bottom wall 222.

A transverse pin 215 is fixed in and extends radially beyond a transverse hole 216 diametrically located in the tail 213 near its bottom end. The protruding ends of the pin 215 extend through and radially beyond diametrically opposed, axially extended slots 217 (FIGS. 4 and 5) in the lower cup 218 of the poppit 214. The slots 217 permit free upward displacement of the piston 202 with respect to the poppit 214. A lower helical compression spring 226 snugly but slidably surrounds the cup 218 of the poppit 214. The spring 226 is axially trapped between the flange 220 and a washer 228 which axially slideably surrounds the cup 218 and is trapped between the spring 226 and the outer ends of the pin 215. The spring 226 axially urges the poppit against the motor head 204.

A further helical compression spring 227 is axially trapped between the step 195 and upper, pumping head 203 so as to continuously resiliently urge the piston 202 and poppit 214 downward against the bottom end cap 193. The upper spring 227 is snugly but slidably received within the main bore 194.

The bottom end cap 193 is fixed to the bottom of the body 191 in sealed relation, here by snap fit telescoping over the bottom portion of the body 191 with an O ring seal 230 (FIG. 4) sandwiched between the bottom of the body 191 and upward facing step 231 on the bottom end cap. The bottom end cap 193 has a central upstanding boss defining an upward facing horizontal exhaust gas valve seat 232. The upper spring 227 normally presses the poppit bottom 222 downwardly against the seat 232 to close an exhaust port 233 extending coaxially downward therethrough and in free communication with the exhaust fitting 33, which opens thereto and extends downward from the bottom end cap 193.

An upward opening annular recess 234 is formed in the top of the bottom end cap 193 and loosely surrounds the exhaust gas valve seat 232. The pressure gas fitting 34, which depends downward from the bottom end cap 193 and is located eccentrically thereof, communicates at its upper end through a restrictive orifice 235 with the annular groove 234 and thus with the lower pressure gas chamber 212 surrounding the poppit 214.

Liquid inlet and outlet check valves 240 and 241 permit liquid flow from the inlet liquid fitting 40, through the bore 196 and frustoconical portion 197 and into the top end cap 192 but prevent opposite flow. The check valves 240 and 241 cooperate with the pumping head 203 to form a pulsing liquid pump. The check valves 240 and 241 are, for example, conveniently provided as flap valves in the manner shown in FIG. 4. Flap valves conveniently occupy very little space and can be made and housed inexpensively. Conventional flap valves comprise a disk of moderately flexible material, as illustrated for example with respect to the flap valve 240 of FIGS. 4 and 4A, having a flexible, centrally located tongue 242 formed by a generally C-shaped slit 243 through the thickness of the material of the flap valve.

A stepped recess 244 in the front side of the pump casing 190 opens into the bore 196 and snugly receives the flanged outlet end 245 of the liquid inlet elbow 40. The outflow end 245 of the elbow 40 is fixed within the recess 244 by in the convenient means, for example the conventional adhesive bonding. To help fix the elbow 0 reliably in the recess 244 (FIG. 4), a stub 247 fixed on the belled lower end 41 of the elbow 40 is snugly received in a blind hole 248 in the opposed front side of the pump body 191 and may be secured therein by any convenient means such as adhesive bonding. The perimeter of the flap valve 240 is fixedly trapped between the elbow end 245 and the step 246 of the recess 244. The perimeter of the corresponding flap 242 is backed on its exterior face by a portion of the flanged end 245 of the elbow 40 to prevent the flap 242 from bending rightwardly (outwardly) past its flat solid line position of FIG. 4, in which position the flap valve 240 is closed. On the other hand, the diameter of the step 246 is sufficient to free the flap 242 to resiliently bend inward as indicated in broken lines in FIG. 4, in response to pressure in the elbow 40 exceeding the vacuum in the bore 196 and frustoconical portion 197, to open the valve 240 and admit liquid from the elbow 40 into the bore 196.

In the embodiment shown, the outlet check valve 241 is constructed and mounted similarly to the above described inlet check valve 240, but of course is arranged for permitting outflow upwardly out of the liquid chamber 196, 197. In the embodiment shown, the depending skirt 250 of the top end cap 192 is snap fitted down into the recess 200 at the upper end of the casing 190 to clamp the perimeter of the outlet flap valve 241 downward against the annular bottom 251 of the recess 200. The bottom 251 extends radially inward sufficient to support the perimeter portion of the corresponding flap 242 so that it cannot bend downward beyond its solid line position shown in FIG. 4. The internal diameter of the skirt 250 is large enough to clear the flap 242 and permit it to bend upwardly, as indicated in broken line in FIG. 4. Accordingly, the outlet check valve 241 permits the flow of liquid in only one direction there: through, namely upward (with the flap bent upward as shown in broken line 242 in FIG. 4).

The upper end of the top end cap 192 receives the corresponding end of the hose 50 in an annular recess, snugly and sealingly telescoped over an upstanding nipple 252 defining the central portion of such annular recess and communicating with the top end of the interior spaced 253 of the top end cap 192.

In addition to the pin-like stubs 16 above-described, an additional pin-like stub 260, protruding laterally inward from the over-under bracket 54, may cooperate with a suitable socket now shown in the rightward part 14 of the housing to further lock the housing parts in registry together. If desired, other ones of the above-described stubs may be utilized for this same purpose of assisting registration of the two housing parts, for example anvils 75 and 102 may cooperate with complimentary parts (not shown) laterally opposing the same and fixed on the innerface of the rightward housing part 14. Using the various stubs 16, 260, etc., the two housing parts, with the remainder of the apparatus properly located therein, can be permanently bonded together. Pin-like stub 261 (FIG. 7) in a stop post to prevent the tip release button 173 from bending inwardly so far as to break off at the hinge, when handpiece is assembled.

The apparatus above-described is preferably constructed of surgical grade materials. For example, the housing 11, trigger 71, pump parts 190, 192, 193, and 202, the fitting 51, the connector 120, the thumb button 103, the insert 127 and the body 128 may be molded of surgical grade ABS. The poppit may be of a suitable plastic material, for example a material sold under the trademark Santoprene. The elbow 40 may be, for example of high impact polystyrene. Metal elements are preferably of stainless steel. Flexible tubing is preferably of soft PVC or latex. The tubes 144 and 153 of the barrel extension 126 are preferably of butyrate or rigid PVC.

Figure 11:
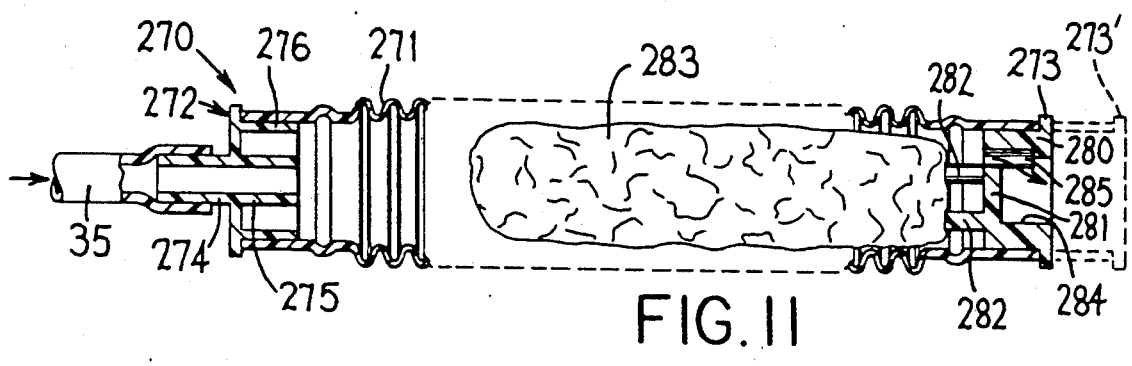
FIG. 11 is a central cross-sectional view of an exhaust gas muffler usable with the FIG. 1 handpiece.

In the preferred embodiment shown, the exhaust line 35 terminates in a muffler 270 (FIG. 11) intended to muffle the sound of exhaust air. The muffler is locatable distance (for example six feet) from the surgical site, by use of a suitably elongate exhaust hose 35. The muffler 270 in the preferred embodiment shown comprises a flexible, elongate, circular cross-section accordion sleeve 271 of suitable resilient plastic material, corrugated over the major central length thereof and cylindrical at the ends thereof for telescoped reception therein of inlet and outlet end caps 272 and 273.

- The inlet end cap 272 has central coaxial inner and outer nipples 274 and 275, the exhaust hose 35 being snugly sleeved over the exterior nipple 274. The internal annular flange 276 snugly and fixedly receives thereover the adjacent end of the sleeve 271.

The outlet end cap 273 is generally cup-shaped, having an annular side wall 280 over which is snugly and fixedly sleeved the remaining end of the sleeve 271. A recessed radial end wall 281 closes the axial inner end of the cup-shaped outlet end cap 273. Circumferentially distributed axial spacers 282, here three in number, extend from the end wall 281 axially into the interior of the sleeve 271. A loose mass 283 of randomly distributed fiber, for example synthetic fiber such as Dacron (TM), partially fills the sleeve 271. Passages 285 pierce the end wall 281 and side wall 280 of outlet end cap 271.

Exhaust gas flows from the tube 35 into the corrugate accordion shell 271, diffuses through the mass of fibrous material 283 and exits through the passages 285 in the dished central recess 284 of the outlet end cap 273. The pressure gas escapes from the pump portion of the motor intermittently, i.e., in a pulsed fashion. The wave fronts of the pulses are substantially reduced in amplitude and sharpness by the damping provided by the fibrous mass 283 and also by the axial expandability of the corrugated, accordion-like shell 271 (particularly note the typical solid line retracted position 273 and expanded position 273' of the outlet end cap, corresponding to the contracted and axially expanded conditions of the accordion-like shell 271). The result is a relatively smooth, quiet exhaust flow out of the recess 284 of the outlet end cap 273 as compared to a relatively noisy pulsed air outflow which would exit from the exhaust tube 35 if the muffler 270 were not present.

OPERATION

The operation of the apparatus will be apparent from the foregoing description. However, aspects of the operation are summarized below for convenient reference.

The pump 20 (FIG. 4) is readily assembled by axially inserting the piston 202, poppit 214, and associated springs 226 and 227 upward into the bottom of the body 191 and adding the lower end cap 193. The check valves 240 and 241 are installed and held in place by installation of the overlying elbow 40 and overlying top end cap 192 respectively. Thereafter the adjacent ends of the hoses 35, 36, 42 and 50 are slid into place as shown in FIG. 4. Adding the fitting 51 to the free end of the hose 50 completes assembly of the FIG. 4 pump.

Thereafter, the assembled pump 20, together with the suction hose 100, fitting 120, trigger unit 70 and thumb button 103 are installed in the left housing part 15 in the manner shown in FIG. 2 and above discussed. This includes insertion of the forward end of the suction hose 100 and fitting 51 into the over-under bracket 54 as above discussed with respect to FIGS. 2 and 9.

The right housing part 14 can then be placed in registry on the left housing part 15 and its contents are held in place thereon by mechanical snaps fit with the possible aid of adhesive bonding.

With the tip unit 125 assembled in the manner above discussed with respect to FIGS. 8-10, the tip unit 125 can be releasably installed in the front end of the barrel 13 and held latched therein by means of the latch unit 160.

Attention is directed to the operation of the pump 20 (FIGS. 4, 6A and 6B). FIG. 4 indicates the normal rest condition of the pump. Gas under pressure (preferably filtered air) continuously feeds from the hose 36 through the restrictive orifice 235 limits the amount of air that can feed from the hose 36 into the pressure gas chamber 212 in the hereinafter described last portion of the operational cycle illustrated in FIG. 6B, namely with the poppit 214 shifted up off its seat 232. On the other hand, the orifice 235 is of sufficient size to admit here to the pressure gas chamber 212 fast enough to cycle the reciprocation of the piston at the desired rate. In one example, the restrictive orifice had a diameter of 0.040.

Pressurized air entering the pressure gas chamber 212 raises the upward pressure on the motor head 204 and gradually raises the piston 202 against the force of the upper spring 227. If the upper (liquid) chamber 196, 197 is filled with liquid, as it would be during ongoing operation of the pump, then the rising pumping head 203 will push liquid against the valve flap 242 of check valve 241 and open same to deliver liquid through the top end cap 192, hose 50, fitting 51, to and through the FIG. 9 tip unit 125 to squirt forwardly from the nozzle 154. At the same time when the piston 202 moves upward the other valve flap 242 of the check valve 240 closes against a portion of wall 245 of elbow 40 so as to prevent liquid from exiting through elbow 40.

Continued rising of the piston 202 continues this action and eventually the piston reaches its FIG. 6A position with the motor head 204 spaced well above the poppit 214 and the piston mounted pin 215 near but out of contact with the upper end of the slots 217 in the opposed sides of the poppit cup 218. In this position the pressure in the pressure gas chamber 212 is virtually at its maximum and the upper spring 227 is nearly fully compressed. The liquid pumping chamber 196, 197 is substantially at minimum volume such that more liquid has been continuously driven therefrom out the nozzle 154 (FIG. 9) as the piston 202 advanced upward from its FIG. 4 to its FIG. 6A position. In addition, during that upward rise of the piston, the lower spring 226 has become further compressed due to the rise of the pin 215 along the slots 217 in the poppit 214.

Note that the middle chamber 211, defined between the piston heads 203 and 204 still is vented through the vent 209 despite the upward rise of the piston 202, such that if air should unexpectedly and accidentally leak upward past the piston motor head 204, such air would be vented through the vent 209 before it could build up in pressure to any level sufficient to leak upward past the pump head 203 and into the liquid chamber 196, 197. Thus, there is no possibility of pressurized air emerging from the nozzle 154 (FIG. 9) in the barrel extension 126.

The piston 202, having risen to the FIG. 6A position, has now nearly brought the poppit 214 to a condition of instability. The poppit 214 in FIG. 6A is still resting upon and closing the exhaust gas valve seat 232 and is held down upon such seat 232 by the pressure of air in the pressure gas chamber 212, which pressure is applied through the slots 217 to atop the closed bottom wall 222 of the poppit 214 and also through axial passages 221 to atop flange 220 of poppit 214. The downward gas pressure on the poppit bottom wall 222 and top flange 220 has firmly held down the poppit 214 to close the exhaust valve seat 232 during the rise of the piston from its FIG. 4 starting position to its FIG. 6A position. However, in the FIG. 6A position the lifting force of the increasingly compressed spring 226 has risen almost to the level required to overcome the downward force on the poppit due to air pressure atop the poppit bottom wall 222 and top flange 220. The poppit is thus closely approaching vertical instability.

In the slight additional rise of the piston 202 from its FIG. 6A to its FIG. 6B position, the additional minor compression of the spring 226 causes the upward spring force on the poppit 214 to exceed the downward force of gas pressure holding the bottom 222 of the poppit closed downward on the exhaust seat 232. As a result, the spring 226 lifts the poppit 214 slightly off the valve seat 232. Therefore, pressurized air in the pressure gas chamber 212 starts to leak out through the exhaust port 232. Gas pressure within the chamber 212 thus drops rapidly. The downward gas force on the poppit and the upward gas force on the piston head 204 thus diminishes rapidly. The spring 226 thus rapidly lifts the poppit 214 up from its FIG. 6B position and the spring 227 forces the piston 202 downward and the two abut at an intermediate position of the distance shown in FIG. 6B between the piston head 204 and the top of the poppit 214. In other words the poppit 214, as soon as it reaches instability, virtually instantaneously "pops" open. Thus gas pressure in the chamber 212 very rapidly drops to atmospheric pressure by exhausting air out the open port 233. As air pressure rapidly drops in the chamber 212 the down force of the compressed upper spring 227, pushing down on the piston, quickly more and more exceeds the up force on the piston due to air pressure in the chamber 212, with the result that the piston 202 is accelerated downward by the vertically expanding spring 227. This downward acceleration of the piston 202 by the spring 227 even more rapidly drives the remaining excess gas from the chamber 212 through the open exhaust port 233. The downwardly accelerating piston 202, by reason of its lower (motor) head 204 bearing on the top of the poppit 214, returns the poppit downwardly as well. The piston 202 and poppit 214 thus move downwardly toward their FIG. 4 starting position.

During the time when the exhaust port 233 is open, air from the compressed air source can still enter the chamber 212 from the fitting 34. However, the rate of flow of pressure air into the chamber 212 is limited by the restrictive orifice 235. Therefore, the loss of air from the compressed air fitting 34 out the open exhaust port 233 is minimized and does not represent a significant energy loss. The downward stroke of the piston 202 and poppit 214 ends when the poppit reaches and closes the exhaust port 233, i.e., when the piston and poppit have returned fully to their FIG. 4 starting position.

The foregoing describes one cycle of operation of the pump 20. It will be understood that the pump continues to cycle in the above manner while adequate air under pressure is supplied at the fitting 34 and liquid is free to flow out the nozzle 154 (FIG. 9).

As the piston 202 moves downward, the pressure in the chamber 196, 197 is correspondingly reduced, which pulls closed the outlet check valve 241 and pulls open the inlet check valve 240 to admit further irrigant liquid to the liquid chamber 196, 197 above the pumping head 203 of the piston 202. The check valves 240 and 241 continuously cycle with the rise and fall of the piston to pass a series of liquid pulses out the nozzle 154 (FIG. 9).

In starting operation of the pump 20 initially, with the liquid tube 42 connected to a liquid source but without it having liquid drawn into the elbow 40, continued operation of the pump (reciprocating of the piston 202 and cycling of the valves 240 and 241) will pump air from the elbow 40, dropping the pressure in the elbow 40 to tend to draw liquid thereinto. It has been found that the pump will self prime from a source several feet below it in this manner.

In one apparatus constructed according to the invention, an air pressure source of 80 to 125 PSI was employed. With about 125 PSI air applied to the tube 36 at its inlet end (not shown), and with the trigger 71 fully pulled to fully open the liquid output tube 50, a maximum flow rate of 900 to 1000 ml per minute of liquid, the latter corresponding to about 1000 pulses per minute of irrigant liquid, was achieved. Flow rate and pulses per minute are both reduced when the tube 50 is only partially opened (the trigger is only partially pulled), or the air pressure in line 36 is reduced. Flow rate and pulse rate are reduced to about half the above described rate (to about 500 ml per minute and 500 pulses per minute), when the air pressure applied to the remote end of the tube 36 is about 80 PSI, in the example above discussed.

Thus, gradual pulling of the trigger gradually increases both the irrigant liquid flow rate and pulse rate.

With the handpiece 10 connected to suction source S, exhaust means E, pressure air source P, and irrigant liquid source L, the trigger 71 will normally be in its dotted line "off" position to close the irrigant liquid hose 50. The thumb button 103 will normally be in its solid line "on" position. The surgeon can insert the forward end of the barrel extension 126 (FIG. 9) into proximity with a surgical site and can apply pulsed irrigation liquid and/or apply suction to draw away the debris, as desired.

Progressively pulling in the trigger 71 toward its solid line position in FIG. 2 progressively unclamps the pulsed irrigation hose 50 to provide the desired frequency and volume of pulsed irrigant flow through the nozzle 154 (FIG. 9) toward the surgical site. The trigger 71 can be, if desired, locked in its solid line, fully open position of FIG. 2, in the manner above discussed.

The suction button 103 can be pushed in and down to lock and block suction off, as discussed above. Lifting the rear end of the thumb button 103 unlocks it and the user can reduce thumb pressure on the thumb button 103 to allow it to progress rearwardly toward its solid line FIG. 2 position. This gradually unblocks the suction hose 100 and provides progressively stronger suction at the front end of the large tube 144 of FIG. 9 to remove debris from the surgical site.

After completion of the surgical procedure on the patient, the handpiece 10 (if desired along with its associated hoses 124, 35, 36 and 42) is intended to be discarded, so as to minimize the possibility of contamination of a later patient.

Although a particular preferred embodiment of the invention has been disclosed in detail for illustrative purposes, it will be recognized that variations or modifications of the disclosed apparatus, including the rearrangement of parts, lie within the scope of the present invention.

We claim:

1. A surgical irrigation handpiece, comprising:
a piston-like housing having a handle and a barrel extending forwardly from the top of said handle at an angle;
a finger actuable trigger adjacent the joinder of said handle and barrel;
an axially elongate pulsing motor/pump unit confined in said handle and extending longitudinally from near the handle bottom to near the top of said handle, said motor/pump unit including a motor in the bottom portion of said handle and a pump in the top portion of said handle,
means inside the bottom of said handle for directing a (1) a high pressure gas supply to the adjacent bottom portion of said motor and (2) an irrigation liquid supply to said pump, the latter means being arranged to effect connection of said motor and pump to supply tubes from respective remote pressure gas and irrigation liquid sources; and
an outlet tube extending from the top of said pump into said barrel and forward toward the front end of said barrel, said trigger controlling pulsed liquid outflow of said pulsing pump through said outlet tube.

2. The device of claim 1 in which said pulsed liquid outlet tube is compressible, said trigger having tube compression means adjacent to the pump to normally compress said tube and thereby normally prevent flow of liquid from said pump therethrough, said trigger being manually squeezable to progressively release said tube compression means and start and increase liquid flow through said tube from said pump.

3. The device of claim 1 comprising a compressed gas inlet port and a gas exhaust port at the bottom of said pump and just above the handle bottom wall, and elongate supply tubes connectable to remote gas and liquid sources and communicating with said ports said directing means comprising holes in the bottom wall of said handle for coupling said tubes to said motor.

4. The device of claim 3 including a further hole in the bottom of said handle, an irrigation liquid supply hose extending through that further hole into the bottom portion of said handle and up within the front portion of said handle, in front of said motor/pump unit, to a liquid inlet port near the top of said pump.

5. The device of claim 1 in which said directing means includes a continuous pressure gas input to said motor for keeping said motor under continuous driving pressure, said trigger being movable to change the outflow rate through said outlet tube of pulsed irrigation liquid and thereby change the operating speed of the motor.

6. The device of claim 1 in which said pump is a continuous run, pulsing output pump which provides continuously pulsed output of liquid for the duration of a single trigger depression said motor including a chamber, a movable poppit member and a movable piston in said chamber, a gas exhaust port normally closed by said poppit member and means responsive to feeding a sufficient amount of pressure gas to said chamber for snapping said poppit member away from said exhaust port and quickly returning said piston member to a starting position to provide a sharp transition in irrigation liquid pressure in said output tube.

7. The device of claim 1 including means on said housing movably mounting said trigger, means on said pump for urging said trigger forward with respect to said handle, means on said trigger normally pinching said outlet tube for blocking flow therethrough, said trigger being moveable rearward for releasing said pinching.

8. The device of claim 1 including a thumb actuable button at the upper rear corner of said barrel above said handle, exterior and interior suction tubes joined by a releasable tube connector trapped in a hole in the bottom part of said handle, the interior suction tube being flexible and extending up in the rear part of said handle close behind the motor/pump unit and past said button and forward through the forward end of said barrel adjacent said liquid outlet tube, such that pressing said button shuts off said suction tube.

9. The device of claim 8 including anvils fixed inside said housing opposite said button and trigger for cooperating therewith to shut off said suction and liquid outflow tubes respectively.

10. The device of claim 1 in which said motor/pump unit is a self-contained closed cartridge insertable as a preassembled unit in said handle, said cartridge including a motor, a pump driven thereby said liquid outlet tube, an irrigant liquid inlet tube to said pump, and elongate energy supply leads to said motor for energizing said motor.

11. The device of claim 10 in which said housing is of split type having right and left parts the right and left parts of said housing being of molded plastic, said right and left housing parts having opposed interior walls and stubs extending from at least one of said interior walls into the interior of said housing and engaging with aid pump for rigidly locating said pump in said housing upon putting together of said right and left housing parts.

12. The device of claim 11 including a thumb actuable button and a resilient suction hose, further stubs for movably locating said trigger and button opposite to respective ones of said anvils and respectively across said suction tube and outlet tube, said trigger and button being cooperable with the respective anvils for pinching and turning off flow through said suction tube and outlet tube respectively.

13. The device of claim 1, including a noise muffler, said pulsing pump being powered by pressure gas and having a pulsing pressure gas exhaust port, means connecting said muffler to said pump pressure gas port for receiving exhaust gas pulses therefrom, said muffler comprising an elongate hollow member having a resiliently extensible and contractible, accordion-like, bellows portion, said bellows portion being interposed between the muffler inlet and a perforated outlet portion of the muffler, fibrous means exposed within said muffler between the inlet and outlet portion thereof and cooperating with the resiliently extensible and contractible bellows portion to smooth the gas pulses emitted from said pump and thereby quiet the flow of pressure gas emitted from said muffler.

14. A pressure gas powered, pulsed output, surgical irrigation handpiece, comprising:
a housing;
a finger actuable trigger movable on said housing for controlling irrigation liquid flow out of said handpiece;
a motor/pump casing in said housing and having a pressure gas inlet port and a gas exhaust port;
a piston axially slidable in said motor/pump casing away from said inlet port in response to increased gas pressure;
a poppit axially slidable in said motor/pump casing and axially slidable with respect to said piston and normally positioned to block said exhaust port;
means responsive to feeding a sufficient amount of pressure gas through said inlet in said motor/pump casing for snapping said poppit away from said exhaust port and quickly returning said piston member to a starting position in a manner to provide a sharp transition in irrigation liquid pressure in said outlet tube;
a pumped irrigation liquid chamber in said motor/pump casing forward of said piston and means for controlling the flow of pump liquid through said chamber in response to reciprocation of said piston;
outlet tube means extending from said pumped liquid chamber for outputting a pulsed irrigation liquid output.

15. A device of claim 14 in which said means for snapping comprises first spring means for urging said piston toward said exhaust port for rapid exhausting of pressure gas between said piston and exhaust port when the latter is open, second spring means urging said poppit towards the piston and away from said exhaust port, means effecting a lost motion connection between said piston and poppit and arranged for causing said poppit to close said exhaust port as the piston returns to its starting position closest to the exhaust port.

16. The device of claim 14 which said piston comprises two axially spaced heads, said casing having a gas escape port communicating with the space between said heads to prevent gas under pressure from entering said liquid chamber from the axial space between said heads.

17. The device of claim 14 in which said casing has a gas exhaust port with a seat normally closed by said poppit, means defining an axial lost motion connection between said piston and poppit, and means responsive to approach of said piston to a forward position for shifting said poppit forward off said seat to open said casing to said gas exhaust port.

18. The device of claim 14 including means defining anon-valved, continuously open, pressure gas inlet passage extending to said casing and opening directly through said casing behind said piston to continuously supply pressure gas to the rear face of said piston.

19. The device of claim 1 in which the trigger is mounted in the top front portion of the handle, close in front of said pump and extending through a substantial portion of the height of said pump, said irrigation liquid supply to the pump comprising a tubular member extending from the bottom of the handle up the front portion of the handle close in front of said motor and connected to the bottom portion of the pump, said trigger closely overlying the top of said irrigation liquid supplying tubular member.

20. The device of claim 19 in which a compression spring is mounted at its opposite lower portion of the trigger to urge the trigger forwardly, thereby outwardly of the housing and away from said pump, to resiliently urge the trigger to its irrigation liquid, "off" position.

21. The device of claim 1 including a tip unit removably fixed on the front end of the barrel, said tip unit including means for releasably securing the tip unit to the barrel and an irrigation tube releasably and sealingly securable to the front end of said outlet tube and extending forward beyond the front end of the barrel for bringing pulsed irrigation liquid flow into a surgical site, a suction hose connectable at one end to a suction source and extending within said housing to a front end adjacent the front end of said barrel, said removable tip unit including a large diameter tube protruding forward from said barrel and communicating with the front end of said suction hose, said removable tip unit establishing a releasable connection between suction hose and large diameter tube, said irrigation tube and large diameter tube extending forward from said barrel with said irrigation tube disposed loosely within said large diameter suction tube.

22. The apparatus of claim 21 including an exchangeable nozzle on the front end of said irrigation tube and means on the front end of said irrigation tube for stabilizing same within said large diameter suction tube.

23. A surgical irrigation handpiece, comprising:
a pistol-like housing having a handle on a barrel extending forwardly from the top of the handle at an angle;
a finger actuable trigger movable with respect to said housing for controlling irrigation liquid flow;
a motor/pump unit in said handle;
an outlet tube extending from the pump outlet end of said motor/pump unit forward toward the front end of said barrel, said trigger controlling irrigation liquid outflow from the pump/motor unit through said outlet tube;
a tip unit removably fixed on the front end of the barrel and including means for releasably securing the tip unit to the barrel and an irrigation tube releasably and sealingly securable to the front end of said outlet tube and extending forward beyond the front end of the barrel for bringing pulsed irrigation liquid flow into a surgical site;
a suction hose connectable at one end to a suction source and extending within said housing to a front end adjacent the front end of said barrel, said removable tip unit including a large diameter tube protruding forward from said barrel and communicating with the front end of said suction hose, said removable tip unit establishing a releasable connection between said suction hose and large diameter tube, said irrigation tube and large diameter tube extending forward from said barrel with said irrigation tube disposed eccentrically within said large diameter suction tube.

24. The apparatus of claim 23 including an exchangeable nozzle on the front end of said irrigation tube and means on the front end of said irrigation tube for stabilizing same within said large diameter suction tube.

25. The device of claim 23 including a suction tube provided in said housing and extending toward the front end of the barrel, the front end of the barrel including support means for fixedly locating the front ends of the outlet tube and suction tube, said removable tip unit having a member establishing of fluid connections with said outlet tube and suction tube, said tip unit having means for guiding same into proper location on the front end of said barrel and having a latch tongue extending into said barrel and latching over a protrusion therein, said barrel including a thumb button actuable to release said protrusion from said latch tongue.

26. A surgical irrigation handpiece, comprising:
a pistol-like housing having a handle and a barrel extending forwardly from the top of the handle at an angle;
a finger actuable trigger adjacent the joinder of the handle and barre;;
an axially elongate pulsing motor/pump unit confined in said handle and extending longitudinally of said handle and including a motor and a pump driven by the motor and having an output for pulsed irrigation liquid adjacent the top thereof;
an outlet tube extending from said outlet of said pump into said barrel and forward along the barrel, said trigger having two compression means adjacent the pump and engageable with said outlet tube, said trigger being manually actuable to progressively release said two compression means and start and increase liquid flow through said tube from said pump;
means for continuously feeding compressed gas to said pump for energizing said pump in a continuous manner such that said pump is under continuous full operating pressure and capable of causing said pump to emit a full irrigation liquid pulse upon opening of said compressible output tube by a momentary actuation of said trigger and without need to build up irrigation liquid pulse pressure over several pulses following actuation of said trigger.

27. The apparatus of claim 26 in which the compressed gas supply means to the motor includes a compressed gas inlet port at the bottom of the pump and means continuously connecting said motor port to a remote pressure gas source of continuous time.

* * * * *

UNITED STATES PATENT AND TRADEMARK OFFICE
CERTIFICATE OF CORRECTION

PATENT NO. : 5 046 486
DATED : September 10, 1991
INVENTOR(S) : David H. GRULKE et al It is certified that error appears in the above-identified patent and that said Letters Patent is hereby corrected as shown below:

```
Column  9, line 57; change "28" to ---128---.
Column 12, line 25; change "0" to ---40---.
Column 17, line 34; change "piston" to ---pistol---.
Column 18, line  1; after "ports" insert a comma (,).
Column 18, line 49; change "outflow" to ---outlet---.
Column 18, line 53; change "a" (first occurrence) to
                    ---the---.
           line 53; change "a" (second occurrence) to
                    ---the---.
           line 53; after "thereby" insert a comma (,).
           line 58; after "parts" insert a comma (,).
Column 18, line 62; change "aid" to ---said---.
Column 18, line 66; after "including" insert ---anvils
                    fixed inside said housing,---.
Column 19, line 64; delete "casing has a".
Column 20, line  4; change "anon" to ---a non---.
Column 20, lines 19-20; after "opposite" insert
                        ---ends on the front of the
                        pump and the laterly
                        opposing---.
```

UNITED STATES PATENT AND TRADEMARK OFFICE
CERTIFICATE OF CORRECTION

PATENT NO. : 5 046 486

DATED : September 10, 1991

INVENTOR(S) : David H. GRULKE et al

It is certified that error appears in the above-identified patent and that said Letters Patent is hereby corrected as shown below:

```
Column 20, line 47; change "on" to ---and---.
Column 21, line 19; delete "of".
Column 22, line 2; change "barre;;" to ---barrel;---.
Column 22, line 10; change "two" to ---tube---.
          line 13; change "two" to ---tube---.
          line 26; change "supply" to ---feeding---.
          line 29; change "time" to ---type---.
```

Signed and Sealed this

Thirtieth Day of March, 1993

*Attest:*

STEPHEN G. KUNIN

*Attesting Officer*     *Acting Commissioner of Patents and Trademarks*